(12) United States Patent
Pfrengle et al.

(10) Patent No.: US 6,277,857 B1
(45) Date of Patent: Aug. 21, 2001

(54) FUNGICIDAL 7-OXY-AND 7-THIO-SUBSTITUTED-TRIAZOLOPYRIMIDINES

(75) Inventors: Waldemar Pfrengle, Seibersbach; Klaus-Juergen Pees, Mainz, both of (DE)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/405,412

(22) Filed: Sep. 24, 1999

Related U.S. Application Data

(60) Provisional application No. 60/101,689, filed on Sep. 25, 1998.

(51) Int. Cl.[7] .................... C07D 487/04; A01N 43/54
(52) U.S. Cl. ..................... 514/258; 544/263; 544/281
(58) Field of Search ................. 514/258; 544/263, 544/281

(56) References Cited

U.S. PATENT DOCUMENTS 4,567,263 * 1/1986 Eicken et al. .................. 544/263
5,593,996 * 1/1997 Pees et al. .................... 514/258
5,602,137 * 2/1997 Ruhter et al. .................. 514/258

FOREIGN PATENT DOCUMENTS

562615 * 9/1993 (EP) .
1148629 * 4/1969 (GB) .

* cited by examiner

*Primary Examiner*—Mark L. Berch
*Assistant Examiner*—Thomas McKenzie
(74) *Attorney, Agent, or Firm*—Charles F. Costello

(57) ABSTRACT

The novel compounds of formula I:

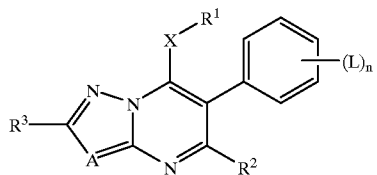

(I)

wherein ($R^1$, $R^2$, $R^3$, A, X, L and n through $L^5$ are defined in the specification) show high fungicidal activity. The new compounds are processed with carriers and adjuvants to fungicidal compositions.

11 Claims, No Drawings

FUNGICIDAL 7-OXY-AND 7-THIO-SUBSTITUTED-TRIAZOLOPYRIMIDINES

This application claims priority from copending provisional application(s) Ser. No. 60/101,689 filed on Sep. 25, 1998.

BACKGROUND OF THE INVENTION

This invention relates to certain triazolopyrimidine compounds, a process for their preparation, compositions containing such compounds, a method for combating a fungus at a locus comprising treating the locus with such compounds and their use as fungicides.

EP-A-0 071 792 claims compounds of the general formula

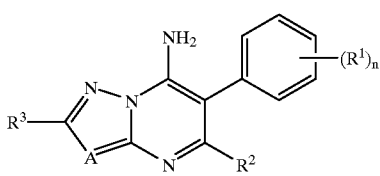

in which $R^1$ represents alkyl, halogen, alkoxy, cyano, cycloalkyl, aryl, aryloxy, arylthio, aralkyl, arylalkyl, arylalkyloxy or arylalkylthio each optionally substituted by halogen or alkoxy; or $(R^1)_n$ represents a benzene, indane or tetrahydronaphthalene ring fused with the phenyl ring, aromatic moieties in the above groups being optionally substituted by alkyl, alkoxy, halogen or cyano; n is 1 or 2; $R^2$ and $R^3$ are each hydrogen, alkyl or aryl, A represents a nitrogen atom or a $CR^4$ group, and $R^4$ is as $R^2$ but can also be halogen, cyano or alkoxycarbonyl or together with $R^3$ can form an alkylene chain containing up to two double bonds. The compounds are said to be active against various phytopathogenic fungi, especially those of the phycomycete class. However evidence of fungicidal activity is only provided for these compounds against *Plasmopara viticola*, a member of the oomycete class of fungi.

U.S. Pat. No. 5,593,996 claims compounds of the general formula

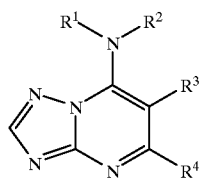

in which $R^1$ represents an optionally substituted alkyl, alkenyl, alkadienyl, cycloalkyl, bicycloalkyl or heterocyclyl group; $R^2$ represents a hydrogen atom or an alkyl group; or $R^1$ and $R^2$ together with the interjacent nitrogen atom represent an optionally substituted heterocyclic ring; $R^3$ represents an optionally substituted phenyl or naphthyl group; and $R^4$ represents a halogen atom or a group —$NR^5R^6$ where $R^5$ represents a hydrogen atom or an amino, alkyl, cycloalkyl or bicycloalkyl group and $R^6$ represents a hydrogen atom or an alkyl group.

The British patent GB 1,148,629 describes a method for the preparation of s-triazolo[1,5-a]pyrimidines which are substituted in the 7-position by a basic group using 7-alkoxy- or 7-alkylthio-s-triazolo[1,5-a]pyrimidines as educts. However, there is no hint to fungicidal activities disclosed.

SUMMARY OF THE INVENTION

The present invention provides a compound of formula I

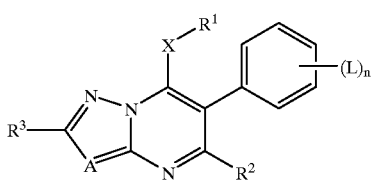

in which
$R^1$ represents an optionally substituted alkyl, alkenyl, alkynyl, alkadienyl, aryl, heteroaryl, cycloalkyl, cycloalkenyl, bicycloalkyl or heterocyclyl group,
$R^2$ represents a halogen atom or a group of formula —Y—$R^4$, wherein Y represents O, S or $NR^5$, with $R^4$ having the meaning given for $R^1$, and $R^5$ being H or forming with $R^4$ and the interjacent nitrogen a heterocyclic ring or having the meaning given for $R^1$,
$R^3$ represents hydrogen or an alkyl or aryl group,
L represents halogen or an optionally substituted alkyl or alkoxy group,
A represents N or $CR^6$, wherein $R^6$ has the meaning given for $R^3$,
X represents O or S, and
n is 0 or an integer between 1 and 5.

The new compounds show an excellent selective fungicidal activity in various crops.

It is an object of the present invention to provide novel, selective fungicidal compounds.

It is also an object of the invention to provide methods for controlling an undesired fungus by contacting said plants with a fungicidally effective amount of the new compounds.

It is another object of the invention to provide selective fungicidal compositions containing the new compounds as active ingredients.

These and other objects and features of the invention will be more apparent from the detailed description set forth hereinbelow, and from the appended claims.

DETAILED DESCRIPTION OF THE PREFERRED EMBODIMENTS

It has surprisingly been found that the compounds of formula I

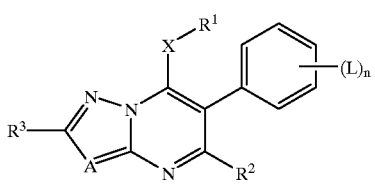

in which $R^1$, $R^2$, $R^3$, A, L and n have the meaning given above for formula I show an excellent fungicidal activity against a broad range of fungi.

In general terms, unless otherwise stated, as used herein the term halogen atom may denote a bromine, iodine, chlorine or fluorine atom, and is especially a bromine, chlorine or fluorine atom. Optionally substituted moieties may be unsubstituted or have from one up to the maximal possible number of substituents. Typically, 0 to 2 substituents are present.

In general terms, unless otherwise stated herein, the terms alkyl, alkenyl, alkynyl, alkadienyl as used herein with respect to a radical or moiety refer to a straight or branched chain radical or moiety. As a rule, such radicals have up to 10, in particular up to 6 carbon atoms. Suitably an alkyl moiety has from 1 to 10 carbon atoms, preferably from 2 to 6 carbon atoms. A preferred alkyl moiety is an ethyl or especially a methyl group. Suitably an alkenyl moiety has from 2 to 6 carbon atoms.

In general terms, unless otherwise stated herein, the term aryl, as used herein with respect to a radical or moiety refers to an aryl group having 6, 10 or 14 carbon atoms, preferably 6 or 10 carbon atoms, in particular phenyl being optionally substituted by one or more halogen atoms, nitro, cyano, alkyl, preferably $C_{1-6}$ alkyl, alkoxy, preferably $C_{1-6}$ alkoxy, haloalkyl, preferably $C_{1-6}$ haloalkyl, haloalkoxy, preferably $C_{1-6}$ haloalkoxy groups.

In general terms, unless otherwise stated herein, the term cycloalkyl or cycloalkenyl, as used herein with respect to a radical or moiety refers to a cycloalkyl group having 3 to 8 carbon atoms or a cycloalkenyl group having 5 to 8 carbon atoms, preferably 5 to 7 carbon atoms, in particular cyclopentyl, cyclohexyl or cyclohexenyl being optionally substituted by one or more halogen atoms, nitro, cyano, alkyl, preferably $C_{1-6}$ alkyl, alkoxy, preferably $C_{1-6}$ alkoxy.

In general terms, unless otherwise stated herein, the term heteroaryl, as used herein with respect to a radical or moiety, refers to an aromatic heterocyclyc group having 5 or 6 ring atoms selected from carbon, nitrogen, oxygen and sulfur, at least one of which being nitrogen, oxygen or sulfur being optionally substituted by one or more halogen atoms, nitro, cyano, alkyl, preferably $C_{1-6}$ alkyl, alkoxy, preferably $C_{1-6}$ alkoxy, in particular azolyl, triazolyl, triazoly, furanyl, oxazolyl, thienyl, thiazolyl, dithiazolyl, pyridyl or pyrimidyl.

In general terms, unless otherwise stated herein, the term heterocyclyl, as used herein with respect to a radical or moiety, refers to a non-aromatic heterocyclyc group having 5 or 6 ring atoms selected from carbon, nitrogen, oxygen and sulfur, at least one of which being nitrogen, oxygen or sulfur being optionally substituted by one or more halogen atoms, nitro, cyano, alkyl, preferably $C_{1-6}$ alkyl, alkoxy, preferably $C_{1-6}$ alkoxy, in particular tetrahydropyranyl, tetrahydrofuranyl, tetrahydrothienyl, tetrahydropyridyl or tetrahydropyrimidyl.

The invention especially relates to compounds of the general formula I in which any alkyl part of the groups $R^1$ which may be straight chained or branched, contains 1 to 10 carbon atoms, preferably 2 to 9 carbon atoms, more preferably 3 to 6 carbon atoms, any alkenyl, alkynyl or alkadienyl part of the substituents $R^1$ contains 2 to 10 carbon atoms, preferably 3 to 9 carbon atoms, more preferably 4 to 6 carbon atoms, any cycloalkyl part of the substituents $R^1$ contains from 3 to 10 carbon atoms, preferably from 3 to 8 carbon atoms, more preferably from 3 to 6 carbon atoms, and any aryl part of the substituents $R^1$ contains 6, 10 or 14 carbon atoms, preferably 6 or 10 carbon atoms, and in which each optionally substituted group independently is substituted by one or more halogen atoms or nitro, cyano, alkyl, preferably $C_{1-6}$ alkyl, cycloalkyl, preferably $C_{3-6}$ cycloalkyl, cycloalkenyl, preferably $C_{3-6}$ cycloalkenyl, haloalkyl, preferably $C_{1-6}$ haloalkyl, halocycloalkyl, preferably $C_{3-6}$ halocycloalkyl, alkoxy, preferably $C_{1-6}$ alkoxy, alkanoyloxy, preferably $C_{1-6}$ alkanoyloxy, haloalkoxy, preferably $C_{1-6}$ haloalkoxy, alkylthio, preferably $C_{1-6}$ alkylthio, phenyl, halo-, dihalo- or trihalophenyl or pyridyl groups. Any alkyl, alkenyl or alkynyl group may be linear or branched. A halogen atom suitably denotes a fluorine, chlorine or bromine atom.

The invention especially relates to compounds of the general formula I in which $R^1$ represents a $C_{1-10}$ alkyl $C_{1-10}$ haloalkyl, in particular a fluorinated $C_{1-10}$ alkyl group, $C_{3-6}$ cycloalkyl, $C_{3-8}$ cycloalkyl-$C_{1-6}$ alkyl, $C_{1-6}$ alkyl-$C_{3-8}$ cycloalkyl, in particular a methylcyclohexyl group, $C_{5-8}$ cycloalkenyl, $C_{1-10}$ alkoxy-$C_{1-6}$alkyl, a phenyl or a mono- or di-$C_{1-6}$ alkyl-phenyl group.

The invention especially relates to compounds of the general formula I in which $R^2$ is a halogen atom, in particular a chloro atom, or an alkoxy group, preferably $C_{15}$ alkoxy, in particular methoxy.

Preferably A represents N and $R^3$ represents a hydrogen atom.

Preferably n is 1, 2 or 3.

Preferably at least one of the substituents L is a fluorine or chlorine atom or a methyl, methoxy or trifluoromethoxy group. The other substituents are preferably selected from hydrogen or fluorine.

Particularly preferred are compounds of formula I, in which the phenyl group of formula

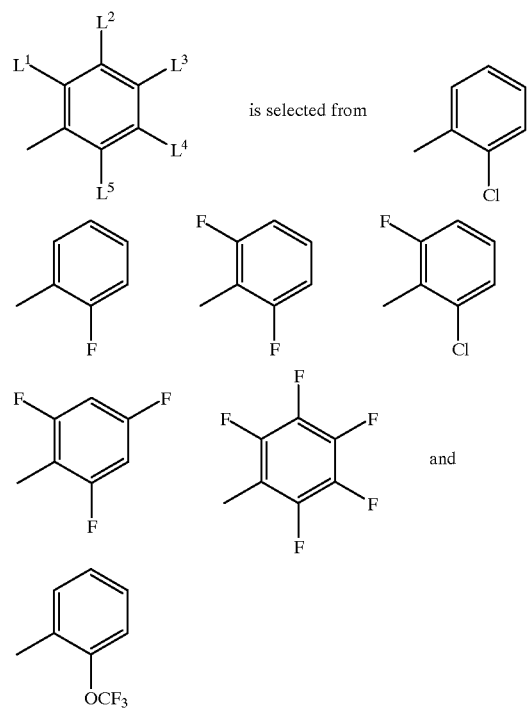

is selected from

Most preferred are the 2-chloro-6-fluorophenyl and the 2,4,6-trifluorophenyl group.

The compounds according to general formula I are oils, gums, or, predominantly crystalline solid materials. They are superior through their valuable fungicidal properties, in particular their fungitoxicity against a broad range of phytopathogenic fungi. For example, they can be used in agriculture or related fields for the control of phytopathogenic fungi such as *Venturia inaequalis, Alternaria solani, Botrytis cinerea, Cercospora beticola, Cladosporium herbarum, Corticium rolfsii, Erysiphe graminis, Helminthosporium tritici repentis, Leptosphaeria nodorum, Micronectriella nivalis, Monilinia fructigena, Mycosphaerella ligulicola, Mycosphaerella pinodes, Phytophthora*

*infestans, Pyricularia grisea f.sp. oryzae, Rhizoctonia solani, Monographella nivalis* and *Scierotinia sclerotiorum*, in particular for the control of *Venturia inaequalis, Alternaria solani* and *Botrytis cinerea*. The compounds of general formula I according to the invention possess a high fungicidal activity within a wide concentration range and may be used in agriculture without any difficulties.

Moreover, the compounds according to the invention show enhanced residual control of fungi compared with conventional fungicides.

Good results in terms of control of phythopathogenic fungi are obtained with a compound as defined in formula I wherein:

$R^2$ represents a chloro atom or a methoxy group;

$R^1$ represents preferably straight chained or branched $C_1$–$C_8$-alkyl, in particular n-propyl, iso-propyl, 1- or 2-methylpropyl, n-butyl, n-pentyl or n-hexyl, $C_{3-7}$-cycloalkyl being optionally substituted by a $C_1$–$C_8$-alkyl group, in particular cyclopentyl, cyclohexyl or 4-methylcyclohexyl, straight chained or branched $C_1$–$C_6$-haloalkyl, in particular 3,3,3-trifluoropropyl, or phenyl being optionally substituted by at least one halogen atom or at least one $C_1$–$C_6$-alkyl or $C_1$–$C_6$-alkoxy group.

In particularly preferred are the compounds of formula IA,

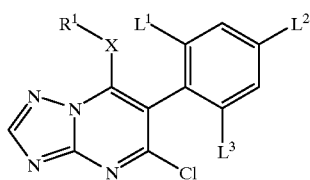

(IA)

in which $R^1$ and X have the meaning given, and $L^1$, $L^2$ and $L^3$ each independently represent hydrogen, fluorine or chlorine, methyl, trifluoromethoxy at least one of which being different from hydrogen.

Especially good results in terms of control of phytopathogenic fungi are obtained by using, for example, the following compounds of formula I: 5-chloro-6-phenyl-7-(furfur-2-ylmethylthio)-[1,2,4]triazolo[1,5-a]pyrimidine, 5-chloro-6-phenyl-7-(3,4,5,6-tetrahydropyrimid-2-ylthio)-[1,2,4]triazolo[1,5-a]pyrimidine, 5-chloro-6-(4-methoxyphenyl)-7-(furfur-2-ylmethylthio)-[1,2,4]triazolo[1,5-a]pyrimidine, 5-chloro-6-(2-chloro-6-fluorophenyl)-7-allylthio-[1,2,4]triazoio[1,5-a]pyrimidine, 5-chloro-6-(2-chloro-6-fluorophenyl)-7-cyclopentylthio-[1,2,4]triazolo[1,5-a]pyrimidine, 5-chloro-6-(2-chloro-6-fluorophenyl)-7-(2,2,2-trifluoroethylthio)-[1,2,4]triazolo[1,5-a]pyrimidine, 5-chloro-6-(2-chloro-6-fluorophenyl)-7-(isopropylthio)-[1,2,4]triazolo[1,5-a]pyrimidine, 5-chloro-6-(2-chloro-6-fluorophenyl)-7-(1-methylpropylthio)-[1,2,4]triazolo[1,5-a]pyrimidine, 5-chloro-6-(2-chloro-6-fluorophenyl)-7-propylthio-[1,2,4]triazolo[1,5-a]pyrimidine, 5-chloro-6-(2-chloro-6-fluorophenyl)-7-(2-methylpropylthio)-[1,2,4]triazolo[1,5-a]pyrimidine, 5-chloro-6-(2-chloro-6-fluorophenyl)-7-cyclohexylthio-[1,2,4]triazolo[1,5-a]pyrimidine, 5-chloro-6-(2-chloro-6-fluorophenyl)-7-butylthio-[1,2,4]triazolo[1,5-a]pyrimidine, 5-chloro-6-(2-chloro-6-fluorophenyl)-7-phenylthio-[1,2,4]triazolo[1,5-a]pyrimidine, 5-chloro-6-(2-chloro-6-fluorophenyl)-7-benzylthio-[1,2,4]triazolo[1,5-a]pyrimidine, 5-chloro-6-(2-chloro-6-fluorophenyl)-7-tert-butylthio-[1,2,4]triazolo[1,5-a]pyrimidine, 5-chloro-6-(2-chloro-6-fluorophenyl)-7-methylthio-[1,2,4]triazolo[1,5-a]pyrimidine, 5-chloro-6-(2-chloro-6-fluorophenyl)-7-ethylthio-[1,2,4]triazolo[1,5-a]pyrimidine, 5-chloro-6-(2-chloro-6-fluorophenyl)-7-(4-chlorophenylthio)-[1,2,4]triazolo[1,5-a]pyrimidine, 5-chloro-6-(2-chloro-6-fluorophenyl)-7-(2-methylphenylthio)-[1,2,4]triazolo[1,5-a]pyrimidine, 5-chloro-6-(2-chloro-6-fluorophenyl)-7-(2-methoxyphenylthio)-[1,2,4]triazolo[1,5-a]pyrimidine, 5-chloro-6-(2-chloro-6-fluorophenyl)-7-(4-methoxyphenylthio)-[1,2,4]triazolo[1,5-a]pyrimidine, 5-chloro-6-(2-chloro-6-fluorophenyl)-7-(2-chlorophenylthio)-[1,2,4]triazolo[1,5-a]pyrimidine, 5-chloro-6-(2-chloro-6-fluorophenyl)-7-ethoxy-[1,2,4]triazolo[1,5-a]pyrimidine, 5-chloro-6-(2-chloro-6-fluorophenyl)-7-cyclopentyloxy-[1,2,4]triazolo[1,5-a]pyrimidine, 5-chloro-6-(2-chloro-6-fluorophenyl)-7-(2,2,2-trifluoroethoxy)-[1,2,4]triazolo[1,5-a]pyrimidine, 5-chloro-7-allylthio-6-(2,4,6-trifluorophenyl)-[1,2,4]triazolo[1,5-a]pyrimidine, 5-chloro-7-cyclopentylthio-6-(2,4,6-trifluorophenyl)-[1,2,4]triazolo[1,5-a]pyrimidine, 5-chloro-7-(2,2,2-trifluoroethylthio)-6-(2,4,6-trifluorophenyl)-[1,2,4]triazolo[1,5-a]pyrimidine, 5-chloro-7-(isopropylthio)-6-(2,4,6-trifluorophenyl)-[1,2,4]triazolo[1,5-a]pyrimidine, 5-chloro-7-(1-methylpropylthio)-6-(2,4,6-trifluorophenyl)-[1,2,4]triazolo[1,5-a]pyrimidine, 5-chloro-7-propylthio-6-(2,4,6-trifluorophenyl)-[1,2,4]triazolo[1,5-a]pyrimidine, 5-chloro-7-(2-methylpropylthio)-6-(2,4,6-trifluorophenyl)-[1,2,4]triazolo[1,5-a]pyrimidine, 5-chloro-7-cyclohexylthio-6-(2,4,6-trifluorophenyl)-[1,2,4]triazolo[1,5-a]pyrimidine, 5-chloro-7-butylthio-6-(2,4,6-trifluorophenyl)-[1,2,4]triazolo[1,5-a]pyrimidine, 5-chloro-7-phenylthio-6-(2,4,6-trifluorophenyl)-[1,2,4]triazolo[1,5-a]pyrimidine, 5-chloro-7-benzylthio-6-(2,4,6-trifluorophenyl)-[1,2,4]triazolo[1,5-a]pyrimidine, 5-chloro-7-tert-butylthio-6-(2,4,6-trifluorophenyl)-[1,2,4]triazolo[1,5-a]pyrimidine, 5-chloro-7-methylthio-6-(2,4,6-trifluorophenyl)-[1,2,4]triazolo[1,5-a]pyrimidine, 5-chloro-7-ethylthio-6-(2,4,6-trifluorophenyl)-[1,2,4]triazolo[1,5-a]pyrimidine, 5-chloro-6-(2,4,6-trifluorophenyl)-7-(4-chlorophenylthio)-[1,2,4]triazolo[1,5-a]pyrimidine, [1,2,4]triazolo[1,5-a]pyrimidine, 5-chloro-6-(2,4,6-trifluorophenyl)-7-(2-methylphenylthio)-[1,2,4]triazolo[1,5-a]pyrimidine, 5-chloro-6-(2,4,6-trifluorophenyl)-7-(2-methoxyphenylthio)-[1,2,4]triazolo[1,5-a]pyrimidine, 5-chloro-6-(2,4,6-trifluorophenyl)-7-(4-methoxyphenylthio)-[1,2,4]triazolo[1,5-a]pyrimidine, 5-chloro-6-(2,4,6-trifluorophenyl)-7-(2-chlorophenylthio)-[1,2,4]triazolo[1,5-a]pyrimidine, 5-chloro-6-(2,4,6-trifluorophenyl)-7-ethoxy-[1,2,4]triazolo[1,5-a]pyrimidine, 5-chloro-6-(2,4,6-trifluorophenyl)-7-cyclopentyloxy-[1,2,4]triazolo[1,5-a]pyrimidine, 5-chloro-6-(2,4,6-trifluorophenyl)-7-(2,2,2-trifluoroethoxy)-[1,2,4]triazolo[1,5-a]pyrimidine.

The present invention further provides a process for the preparation of a compound of formula I, which comprises (a) treating a 5,7-dihalo-triazolopyrimidine of formula II,

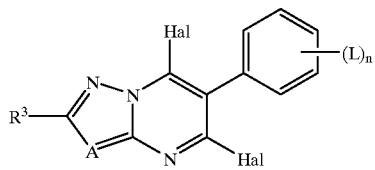

(II)

in which $R^3$, A, L and n have the meaning given for formula I and Hal represents a halogen atom, with a compound of formula III $$R^1-XH \quad \quad (III)$$

in which
$R^1$ and X are as defined for formula I, in the presence of a base.

(b) optionally treating the resulting 5-halogentriazolopyrimidine with an alcohol, or a thiol or amine of formula $R^4-YH$, in which $R^4$ and Y are as defined for formula I, in the presence of a base.

The reaction between the 5,7-dihalo-6-aryl-triazolopyrimidines of formula II, which are known from U.S. Pat. No. 5,593,996, and the compound of formula III is conveniently carried out in the presence of a solvent. Suitable solvents include ethers, such as dioxane, diethyl ether and, especially, tetrahydrofuran, hydrocarbons such as hexane, cyclohexane or mineral oil, and aromatic hydrocarbons, for example toluene, or mixtures of these solvents. The reaction is suitably carried out at a temperature in the range from −100° C. to +100° C., the preferred reaction temperature being from −80° C. to +40° C. It is also preferred that the reaction is carried out in the presence of a strong base. Preferred strong bases are alkalimetal alkanes such as methyllithium, n-butyllithium, tert-butyllithium, or alkalimetal amides such as sodium amide, lithium diisopropylamide or potassium hexadimethylsilazide or alkalimetal hydrides such as sodium or potassium hydride, in particular sodium hydride.

The compounds of general formula I have been found to have fungicidal activity. Accordingly, the invention further provides a fungicidal composition which comprises an active ingredient, which is at least one compound of formula I as defined above, and one or more carriers. A method of making such a composition is also provided which comprises bringing a compound of formula I as defined above into association with the carrier(s). Such a composition may contain a single active ingredient or a mixture of several active ingredients of the present invention. It is also envisaged that different isomers or mixtures of isomers may have different levels or spectra of activity and thus compositions may comprise individual isomers or mixtures of isomers.

A composition according to the invention preferably contains from 0.5% to 95% by weight (w/w) of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including material which is normally a gas but which has been compressed to form a liquid.

The compositions may be manufactured into e.g. emulsion concentrates, solutions, oil in water emulsions, wettable powders, soluble powders, suspension concentrates, dusts, granules, water dispersible granules, micro-capsules, gels and other formulation types by well-established procedures. These procedures include intensive mixing and/or milling of the active ingredients with other substances, such as fillers solvents, solid carriers, surface active compounds (surfactants), and optionally solid and/or liquid auxiliaries and/or adjuvants. The form of application such as spraying, atomizing, dispersing or pouring may be chosen like the compositions according to the desired objectives and the given circumstances Solvents may be aromatic hydrocarbons, e.g. Solvesso® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or γ-butyrolactone, higher alkyl pyrrolidones, e.g. n-octylpyrrolidone or cyclohexylpyrrolidone, epoxidized plant oil esters, e.g. methylated coconut or soybean oil ester and water. Mixtures of different liquids are often suitable.

Solid carriers, which may be used for dusts, wettable powders, water dispersible granules, or granules, may be mineral fillers, such as calcite, talc, kaolin, montmorillonite or attapulgite. The physical properties may be improved by addition of highly dispersed silica gel or polymers. Carriers for granules may be porous material, e.g. pumice, kaolin, sepiolite, bentonite; non-sorptive carriers may be calcite or sand. Additionally, a multitude of pre-granulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

Surfactants may be nonionic, anionic, cationic or zwitterionic substances with good dispersing, emulsifying and wetting properties depending on the nature of the compound according to general formula I to be formulated. Surfactants may also mean mixtures of individual surfactants.

The compositions of the invention may for example be formulated as wettable powders, water dispersible granules, dusts, granules, solutions, emulsifiable concentrates, emulsions, suspension concentrates and aerosols. Wettable powders usually contain 5 to 90% w/w of active ingredient and usually contain in addition to solid inert carrier, 3 to 10% w/w of dispersing and wetting agents and, where necessary, 0 to 10% w/w of stabilizer(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5 to 10% w/w of active ingredient. Water dispersible granules and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents. The so-called "dry flowables" consist of relatively small granules having a relatively high concentration of active ingredient. Emulsifiable concentrates usually contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates are usually milled so as to obtain a stable, non-sedimenting flowable product and usually contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation and crystalization or as antifreeze agents for water.

Aqueous dispersions and emulsions, for example compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected.

The biological activity of the active ingredient can also be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient.

As a commodity the compositions may preferably be in a concentrated form whereas the end user generally employs diluted compositions. The compositions may be diluted to a concentration down to 0.001% of active ingredient. The doses usually are in the range from 0.01 to 10 kg a.i./ha.

Examples of formulations according to the invention are:

| Emulsion Concentrate (EC) | | |
|---|---|---|
| Active Ingredient | Compound of Example 7 | 30% (w/v) |
| Emulsifier(s) | Atlox ® 4856 B/Atlox ® 4858 B[1] (mixture containing calcium alkyl aryl sulfonate, fatty alcohol ethoxylates and light aromatics/ mixture containing calcium alkyl aryl sulfonate, fatty alcohol ethoxylates and light aromatics) | 5% (w/v) |
| Solvent | Shellsol ® A[2] (mixture of $C_9$–$C_{10}$ aromatic hydrocarbons) | to 1000 ml |
| Suspension Concentrate (SC) | | |
| Active Ingredient | Compound of Example 7 | 50% (w/v) |
| Dispersing agent | Soprophor ® FL[3] (polyoxyethylene polyaryl phenyl ether phosphate amine salt) | 3% (w/v) |
| Antifoaming agent | Rhodorsil ® 422[3] (nonionic aqueous emulsion of polydimethylsiloxanes) | 0.2% (w/v) |
| Structure agent | Kelzan ® S[4] (Xanthan gum) | 0.2% (w/v) |
| Antifreezing agent | Propylene glycol | 5% (w/v) |
| Biocidal agent | Proxel ®[5] (aqueous dipropylene glycol solution containing 20% 1,2-benisothiazolin-3-one) | 0.1% (w/v) |
| Water | | to 1000 ml |
| Wettable Powder (WP) | | |
| Active Ingredient | Compound of Example 7 | 60% (w/w) |
| Wetting agent | Atlox ® 4995[1] (polyoxyethylene alkyl ether) | 2% (w/w) |
| Dispersing agent | Witcosperse ® D-60[6] (mixture of sodium salts of condensed naphthalene sulfonic acid and alkylarylpolyoxy acetates | 3% (w/w) |
| Carrier/Filler | Kaolin | 35% (w/w) |
| Water Dispersible Granules (WG) | | |
| Active Ingredient | Compound of Example 7 | 50% (w/w) |
| Dispersing/ Binding agent | Witcosperse ® D-450[6] (mixture of sodium salts of condensed naphthalene sulfonic acid and alkyl sulfonates) | 8% (w/w) |
| Wetting agent | Morwet ® EFW[6] (formaldehyde condensation product) | 2% (w/w) |
| Antifoaming agent | Rhodorsil ® EP 6703[3] (encapsulated silicone) | 1% (w/w) |
| Disintegrant | Agrimer ® ATF[7] (cross-linked homopolymer of N-vinyl-2-pyrrolidone) | 2% (w/w) |
| Carrier/Filler | Kaolin | 35% (w/w) |

[1] commercially available from ICI Surfactants
[2] commercially available from Deutsche Shell AG
[3] commercially available from Rhône-Poulenc
[4] commercially available from Kelco Co.
[5] commercially available from Zeneca
[6] commercially available from Witco
[7] commercially available from International Speciality Products The compositions of this invention can also comprise other compounds having biological activity, e.g. compounds having similar or complementary pesticidal activity or compounds having plant growth regulating, fungicidal or insecticidal activity. These mixtures of pesticides can have a broader spectrum of activity than the compound of general formula I alone. Furthermore, the other pesticide can have a synergistic effect on the pesticidal activity of the compound of general formula I.

The compositions of this invention can comprise also other compounds having biological activity, e.g compounds having similar or complementary fungicidal activity or compounds having plant growth regulating, herbicidal or insecticidal activity.

These mixtures of fungicides can have a broader spectrum of activity than the compound of general formula I alone. Furthermore, the other fungicide can have a synergistic effect on the fungicidal activity of the compound of general formula I.

Examples of the other fungicidal compounds are anilazine, azoxystrobin, benalaxyl, benomyl, binapacryl, bitertanol, blasticidin S, Bordeaux mixture, bromuconazole, bupirimate, captafol, captan, carbendazim, carboxin, carpropamid, chlorbenzthiazon, chlorothalonil, chlozolinate, copper-containing compounds such as copper oxychloride, and copper sulfate, cycloheximide, cymoxanil, cypofuram, cyproconazole, cyprodinil, dichlofluanid, dichlone, dichloran, diclobutrazol, diclocymet, diclomezine, diethofencarb, difenoconazole, diflumetorim, dimethirimol, dimethomorph, diniconazole, dinocap, ditalimfos, dithianon, dodemorph, dodine, edifenphos, epoxiconazole, etaconazole, ethirimol, etridiazole, famoxadone, fenapanil, fenarimol, fenbuconazole, fenfuram, fenhexamid, fenpiclonil, fenpropidin, fenpropimorph, fentin, fentin acetate, fentin hydroxide, ferimzone, fluazinam, fludioxonil, flumetover, fluquinconazole, flusilazole, flusulfamide, flutolanil, flutriafol, folpet, fosetyl-aluminium, fuberidazole, furalaxyl, furametpyr, guazatine, hexaconazole, imazalil, iminoctadine, ipconazole, iprodione, isoprothiolane, kasugamycin, kitazin P, kresoxim-methyl, mancozeb, maneb, mepanipyrim, mepronil, metalaxyl, metconazole, methfuroxam, myclobutanil, neoasozin, nickel dimethyldithiocarbamate, nitrothalisopropyl, nuarimol, ofurace, organo mercury compounds, oxadixyl, oxycarboxin, penconazole, pencycuron, phenazineoxide, phthalide, polyoxin D, polyram, probenazole, prochloraz, procymidione, propamocarb, propiconazole, propineb, pyrazophos, pyrifenox, pyrimethanil, pyroquilon, pyroxyfur, quinomethionate, quinoxyfen, quintozene, spiroxamine, SSF-126, SSF-129, streptomycin, sulfur, tebuconazole, tecloftalame, tecnazene, tetraconazole, thiabendazole, thifluzamide, thiophanate-methyl, thiram, tolclofosmethyl, tolylfluanid, triadimefon, triadimenol, triazbutil, triazoxide, tricyclazole, tridemorph, triflumizole, triforine, triticonazole, validamycin A, vinclozolin, XRD-563, zarilamid, zineb, ziram.

In addition, the co-formulations according to the invention may contain at least one compound of formula I and any of the following classes of biological control agents such as viruses, bacteria, nematodes, fungi, and other microorganism which are suitable to control insects, weeds or plant diseases or to induce host resistance in the plants. Examples of such biological control agents are: *Bacillus thuringiensis, Verticillium lecanii, Autographica californica NPV, Beauvaria bassiana, Ampelomyces quisqualis, Bacilis subtilis, Pseudomonas fluorescens, Steptomyces griseoviridis* and *Trichoderma harzianum.*

Moreover, the co-formulations according to the invention may contain at least one compound of formula I and a chemical agent that induces the systemic acquired resistance in plants such as for example nicotinic acid or derivatives thereof, 2,2-dichloro-3,3-dimethylcyclopropanecarboxylic acid or BION.

The compounds of general formula I can be mixed with soil, peat or other rooting media for the protection of the plants against seed-borne, soil-borne or foliar fungal diseases.

The invention still further provides the use as a fungicide of a compound of the general formula I as defined above or a composition as defined above, and a method for combating fungus at a locus, which comprises treating the locus, which may be for example plants subject to or subjected to fungal attack, seeds of such plants or the medium in which such plants are growing or are to be grown, with such a compound or composition.

The present invention is of wide applicability in the protection of crop and ornamental plants against fungal attack. Typical crops which may be protected include vines, grain crops such as wheat and barley, rice, sugar beet, top fruit, peanuts, potatoes and tomatoes. The duration of the protection is normally dependent on the individual compound selected, and also a variety of external factors, such as climate, whose impact is normally mitigated by the use of a suitable formulation.

The following examples further illustrate the present invention. It should be understood, however, that the invention is not limited solely to the particular examples given below.

EXAMPLE 1
Preparation of 5-chloro-7-(furfur-2-ylmethylthio)-6-phenyl-[1,2,4]-triazolo[1,5a]pyrimidine 1.2 g (0.01 mol) furfurylmercaptan are added to a suspension of 1.3 g NaH (0.01 mol) in tetrahydrofuran (THF) and refluxed for 2 hours. The mixture is cooled down to ambient temperature and 2.6 g (0.01 mol) 5,7-dichloro-6-phenyl-[1,2,4]triazolo[1,5a]pyrimidine are added. The resulting mixture is stirred for 3 hours. The solvent is evaporated, the residue is dissolved in ethyl acetate, the solution is washed with water twice and the organic phase is dried. The solution is filtered, the solvent is evaporated and the residue is purified by flash chromatography, which yields the product as an oil (1.1 g, 32%).

EXAMPLES 2–47

The following examples (Table I; structure and melting point) are synthesized analogously to Example 1.

TABLE I

| Example | $R^1$ | X | $L^1$ | $L^2$ | $L^3$ | melting point (° C.) |
|---|---|---|---|---|---|---|
| 2 | 1,4,5,6-tetrahydropyrimid-2-yl | S | H | H | H | 212 |
| 3 | furfur-2-ylmethyl | S | H | OCH$_3$ | H | oil |
| 4 | allyl | S | F | H | Cl | 95–97 |
| 5 | cyclopentyl | S | F | H | Cl | 105–108 |
| 6 | 2,2,2-trifluoroethyl | S | F | H | Cl | 155–157 |
| 7 | isopropyl | S | F | H | Cl | oil |
| 8 | 1-methylpropyl | S | F | H | Cl | 72–75 |
| 9 | n-propyl | S | F | H | Cl | oil |
| 10 | 2-methylpropyl | S | F | H | Cl | 93–95 |
| 11 | cyclohexyl | S | F | H | Cl | 104–105 |
| 12 | n-butyl | S | F | H | Cl | 71–72 |
| 13 | phenyl | S | F | H | Cl | 129–130 |
| 14 | benzyl | S | F | H | Cl | 143–146 |
| 15 | tert-butyl | S | F | H | Cl | 104–109 |
| 16 | methyl | S | F | H | Cl | oil |
| 17 | ethyl | S | F | H | Cl | 106–117 |
| 18 | 4-chlorophenyl | S | F | H | Cl | 166–172 |
| 19 | 2-methylphenyl | S | F | H | Cl | 102–112 |
| 20 | 2-methoxyphenyl | S | F | H | Cl | 136–140 |
| 21 | 4-methoxyphenyl | S | F | H | Cl | 144–148 |
| 22 | 2-chlorophenyl | S | F | H | Cl | 123–127 |
| 23 | ethyl | O | F | H | Cl | 80–83 |
| 24 | cyclopentyl | O | F | H | Cl | 106–108 |
| 25 | 2,2,2-trifluoroethyl | O | F | H | Cl | 124–127 |
| 26 | allyl | S | F | F | F | |
| 27 | cyclopentyl | S | F | F | F | |
| 28 | 2,2,2-trifluoroethyl | S | F | F | F | |
| 29 | isopropyl | S | F | F | F | |
| 30 | 1-methylpropyl | S | F | F | F | |
| 31 | n-propyl | S | F | F | F | |
| 32 | 2-methylpropyl | S | F | F | F | |
| 33 | cyclohexyl | S | F | F | F | |
| 34 | n-butyl | S | F | F | F | |
| 35 | phenyl | S | F | F | F | |
| 36 | benzyl | S | F | F | F | |
| 37 | tert-butyl | S | F | F | F | |
| 38 | methyl | S | F | F | F | |
| 39 | ethyl | S | F | F | F | |
| 40 | 4-chlorophenyl | S | F | F | F | |
| 41 | 2-methylphenyl | S | F | F | F | |
| 42 | 2-methoxyphenyl | S | F | F | F | |
| 43 | 4-methoxyphenyl | S | F | F | F | |
| 44 | 2-chlorophenyl | S | F | F | F | |
| 45 | ethyl | O | F | F | F | |
| 46 | cyclopentyl | O | F | F | F | |
| 47 | 2,2,2-trifluoroethyl | O | F | F | F | |

Biological Investigations

Determination of Minimum Inhibitory Concentration by Test Compounds in the Serial Dilution Test with Various Phytopathogenic Fungi The MIC (Minimum Inhibitory Concentration) value, which indicates the lowest concentration of the active ingredient in the growth medium which causes a total inhibition of myecelial growth, is determined by serial dilution tests using Microtiter plates with 24 or 48 wells per plate. The dilution of the test compounds in the nutrient solution and the distribution to the wells is carried out by a TECAN RSP 5000 Robotic Sample Processor. The following test compound concentrations are used: 0.05, 0.10, 0.20, 0.39, 0.78, 1.56, 3.13, 6.25, 12.50, 25.00, 50.00 and 100.00 mg/ml. For preparation of the nutrient solution, V8 vegetable juice (333 ml) is mixed with calcium carbonate (4.95 g), centrifuged, the supernatant (200 ml) diluted with water (800 ml) and autoclaved at 121° C. for 30 min. The respective inocula (*Alternaria solani*, ALTESO; *Botrytis cinerea*, BOTRCI; *Leptosphaeria nodorum*, LEPTNO; *Phytophthora infestans*, PHYTIN; *Magnaporthe grisea f.* sp. *oryzae*, PYRIOR; *Pyrenophora teres*, PYRNTE; *Rhizoctonia solani*, RHIZSO) are added into the wells as spore suspensions (50 ml; 5×10$^5$/ml) or agar slices (6 mm) of an agar culture of the fungus. After 6–12 days incubation at suitable temperatures (18–25° C.), the MIC values are determined by visual inspection of the plates (Table II; n.t.=not tested).

TABLE II

| Example | ALTESO | BOTRCI | LEPTNO | PHYTIN | PYRIOR | PYRNTE | RHIZSO |
|---|---|---|---|---|---|---|---|
| 4 | 6.25 | 12.5 | >100 | 100 | n.t. | 100 | 25 |
| 5 | 1.56 | >100 | >100 | >100 | n.t. | >100 | >100 |
| 7 | 6.25 | 1.56 | >100 | >100 | n.t. | 12.5 | 12.5 |
| 8 | 12.5 | 3.13 | 100 | >100 | n.t. | >100 | >100 |
| 9 | 12.5 | n.t. | 50 | >100 | 25 | >100 | >100 |
| 10 | 12.5 | >100 | 25 | >100 | 25 | >100 | >100 |
| 11 | 12.5 | >100 | >100 | 50 | 12.5 | >100 | >100 |
| 12 | 12.5 | >100 | 25 | >100 | 25 | >100 | >100 |
| 16 | >100 | 25 | 100 | >100 | 25 | >100 | >100 |
| 23 | 25 | 25 | >100 | 100 | n.t. | 50 | 25 |
| 25 | 25 | 100 | 100 | 1.56 | n.t. | 12.5 | 100 |

What is claimed is:

1. A compound of formula I:

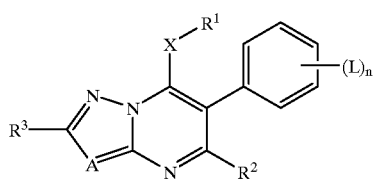

(I)

wherein
- R$^1$ represents an alkyl or an optionally substituted alkenyl, alkynyl, alkadienyl, aryl, heteroaryl, cycloalkyl, bicycloalkyl or heterocyclyl group,
- R$^2$ represents a halogen atom or a group of formula —Y—R$^4$, wherein Y represents O, S or NR$^5$,
- R$^3$ represents hydrogen, or an alkyl or aryl group,
- R$^4$ has the meaning given for R$^1$,
- R$^5$ represents a hydrogen atom or has the meaning given for R$^1$, or
- R$^4$ and R$^5$ together with the interjacent nitrogen atom represent a heterocyclic ring,
- L represents halogen, or an optionally substituted alkyl or alkoxy group,
- A represents N or CR$^6$, wherein R$^6$ has the meaning given for R$^3$,
- X represents O or S, and
- n is 0 or an integer between 1 and 5.

2. A compound of the formula I:

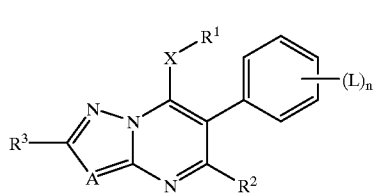

(I)

wherein
- R$^1$ represents an alkyl group substituted with an alkyl, alkenyl, alkynyl, alkadienyl, cycloalkyl, bicycloalkyl or heterocyclyl group,
- R$^2$ represents a halogen atom or a group of formula —Y—R$^4$, wherein Y represents O, S or NR$^5$,
- R$^3$ represents hydrogen, or an alkyl or aryl group,
- R$^4$ has the meaning given for R$^1$,
- R$^5$ represents a hydrogen atom or has the meaning given for R$^1$, or
- R$^4$ and R$^5$ together with the interjacent nitrogen atom represent a heterocyclic ring,
- L represents halogen, or an optionally substituted alkyl or alkoxy group,
- A represents N or CR$^6$, wherein R$^6$ has the meaning given for R$^3$,
- X represents O or S, and
- n is 0 or an integer between 1 and 5.

3. A compound of formula I:

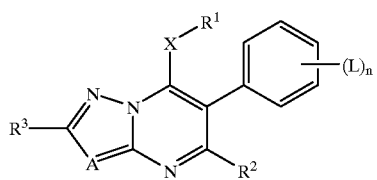

(I)

wherein
- R$^1$ represents an alkyl group substituted with either an aryl or a heteroaryl group,
- R$^2$ represents a halogen atom or a group of formula —Y—R$^4$, wherein Y represents O, S or NR$^5$,
- R$^3$ represents hydrogen, or an alkyl or aryl group,
- R$^4$ has the meaning given for R$^1$,
- R$^5$ represents a hydrogen atom or has the meaning given for R$^1$, or R⁴ and R⁵ together with the interjacent nitrogen atom represent a heterocyclic ring, L represents halogen, or an optionally substituted alkyl or alkoxy group, A represents N or CR⁶, wherein R⁶ has the meaning given for R³, X represents O or S, and n is 0 or an integer between 1 and 5.

4. A compound of formula I:

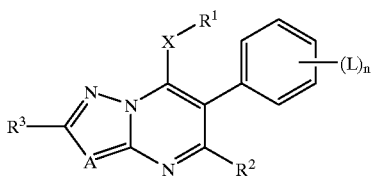

(I)

wherein

R¹ represents an aryl or heteroaryl group substituted with an alkyl group,

R² represents a halogen atom or a group of formula —Y—R⁴, wherein Y represents O, S or NR⁵, R³ represents hydrogen, or an alkyl or aryl group, R⁴ has the meaning given for R¹, R represents a hydrogen atom or has the meaning given for R¹, or R⁴ and R⁵ together with the interjacent nitrogen atom represent a heterocyclic ring, L represents halogen, or an optionally substituted alkyl or alkoxy group, A represents N or CR⁶, wherein R⁶ has the meaning given for R³, X represents O or S, and n is 0 or an integer between 1 and 5.

5. A compound according to claim 1 or 2 or 3 or 4 in which R¹ represents straight or branched chained $C_1$–$C_6$ alkyl, $C_{1-6}$ haloalkyl or $C_2$–$C_6$ alkenyl, $C_3$–$C_8$ cycloalkyl or phenyl, being optionally substituted by at least one substituent selected from the group consisting of halogen, and $C_1$–$C_4$alkyl and $C_1$–$C_4$alkoxy.

6. A compound according to claim 1 or 2 or 4 in which R² represents chlorine.

7. A compound according to claim 1 in which A is N and R³ is hydrogen.

8. A compound according to claim 1 selected from the group consisting of:

5-chloro-6-phenyl-7-(furfur-2-ylmethylthio)-[1,2,4]triazolo[1,5-a]pyrimidine, 5-chloro-6-phenyl-7-(3,4,5,6-tetrahydropyrimid-2-ylthio)-[1,2,4]triazolo[1,5-a]pyrimidine, 5-chloro-6-(4-methoxyphenyl)-7-(furfur-2-ylmethylthio)-[1,2,4]triazolo[1,5-a]pyrimidine, 5-chloro-6-(2-chloro-6-fluorophenyl)-7-allylthio-[1,2,4]triazolo[1,5-a]pyrimidine, 5-chloro-6-(2-chloro-6-fluorophenyl)-7-cyclopentylthio-[1,2,4]triazolo[1,5-a]pyrimidine, 5-chloro-6-(2-chloro-6-fluorophenyl)-7-(2,2,2-trifluoroethylthio)-[1,2,4]triazolo[1,5-a]pyrimidine, 5-chloro-6-(2-chloro-6-fluorophenyl)-7-(isopropylthio)-[1,2,4]triazolo[1,5-a]pyrimidine, 5-chloro-6-(2-chloro-6-fluorophenyl)-7-(1-methylpropylthio)-[1,2,4]triazolo[1,5-a]pyrimidine, 5-chloro-6-(2-chloro-6-fluorophenyl)-7-propylthio-[1,2,4]triazolo[1,5-a]pyrimidine, 5-chloro-6-(2-chloro-6-fluorophenyl)-7-(2-methylpropylthio)-[1 2,4]triazolo[1,5-a]pyrimidine, 5-chloro-6-(2-chloro-6-fluorophenyl)-7-cyclohexylthio-[1,2,4]triazolo[1,5-a]pyrimidine, 5-chloro-6-(2-chloro-6-fluorophenyl)-7-butylthio-[1,2,4]triazolo[1,5-a]pyrimidine, 5-chloro-6-(2-chloro-6-fluorophenyl)-7-phenylthio-[1,2,4]triazolo[1,5-a]pyrimidine, 5-chloro-6-(2-chloro-6-fluorophenyl)-7-benzylthio-[1,2,4]triazolo[1,5-a]pyrimidine, 5-chloro-6-(2-chloro-6-fluorophenyl)-7-tert-butylthio-[1,2,4]triazolo[1,5-a]pyrimidine, 5-chloro-6-(2-chloro-6-fluorophenyl)-7-methylthio-[1,2,4]triazolo[1,5-a]pyrimidine, 5-chloro-6-(2-chloro-6-fluorophenyl)-7-ethylthio-[1,2,4]triazolo[1,5-a]pyrimidine, 5-chloro-6-(2-chloro-6-fluorophenyl)-7-(4-chlorophenylthio)-[1,2,4]triazolo[1,5-a]pyrimidine, 5-chloro-6-(2-chloro-6-fluorophenyl)-7-(2-methylphenylthio)-[1,2,4]triazolo[1,5-a]pyrimidine, 5-chloro-6-(2-chloro-6-fluorophenyl)-7-(2-methoxyphenylthio)-[1,2,4]triazolo[1,5-a]pyrimidine, 5-chloro-6-(2-chloro-6-fluorophenyl)-7-(4-methoxyphenylthio)-[1,2,4]triazolo[1,5-a]pyrimidine, 5-chloro-6-(2-chloro-6-fluorophenyl)-7-(2-chlorophenylthio)-[1,2,4]triazolo[1,5-a]pyrimidine, 5-chloro-6-(2-chloro-6-fluorophenyl)-7-ethoxy-[1,2,4]triazolo[1,5-a]pyrimidine, 5-chloro-6-(2-chloro-6-fluorophenyl)-7-cyclopentyloxy-[1,2,4]triazolo[1,5-a]pyrimidine, 5-chloro-6-(2-chloro-6-fluorophenyl)-7-(2,2,2-trifluoroethoxy)-[1,2,4]triazolo[1,5-a]pyrimidine, 5-chloro-7-allylthio-6-(2,4,6-trifluorophenyl)-[1,2,4]triazolo[1,5-a]pyrimidine 5-chloro-7-cyclopentylthio-6-(2,4,6-trifluorophenyl)-[1,2,4]triazolo[1,5-a]pyrimidine, 5-chloro-7-(2,2,2-trifluoroethylthio)-6-(2,4,6-trifluorophenyl)-[1,2,4]triazolo[1,5-a]pyrimidine, 5-chloro-7-(isopropylthio)-6-(2,4,6-trifluorophenyl)-[1,2,4]triazolo[1,5-a]pyrimidine, 5-chloro-7-(1-methylpropylthio)-6-(2,4,6-trifluorophenyl)-[1,2,4]triazolo[1,5-a]pyrimidine, 5-chloro-7-propylthio-6-(2,4,6-trifluorophenyl)-[1,2,4]triazolo[1,5-a]pyrimidine, 5-chloro-7-(2-methylpropylthio)-6-(2,4,6-trifluorophenyl)-[1,2,4]triazolo[1,5-a]pyrimidine, 5-chloro-7-cyclohexylthio-6-(2,4,6-trifluorophenyl)-[1,2,4]triazolo[1,5-a]pyrimidine, 5-chloro-7-butylthio-6-(2,4,6-trifluorophenyl)-[1,2,4]triazolo[1,5-a]pyrimidine, 5-chloro-7-phenylthio-6-(2,4,6-trifluorophenyl)-[1,2,4]triazolo[1,5-a]pyrimidine, 5-chloro-7-benzylthio-6-(2,4,6-trifluorophenyl)-[1,2,4]triazolo[1,5-a]pyrimidine, 5-chloro-7-tert-butylthio-6-(2,4,6-trifluorophenyl)-[1,2,4]triazolo[1,5-a]pyrimidine, 5-chloro-7-methylthio-6-(2,4,6-trifluorophenyl)-[1,2,4]triazolo[1,5-a]pyrimidine, 5-chloro-7-ethylthio-6-(2,4,6-trifluorophenyl)-[1,2,4]triazolo[1,5-a]pyrimidine, 5-chloro-6-(2,4,6-trifluorophenyl)-7-(4-chlorophenylthio)-[1,2,4]triazolo[1,5-a]pyrimidine, 5-chloro-6-(2,4,6-trifluorophenyl)-7-(2-methylphenylthio)-[1,2,4]triazolo[1,5-a]pyrimidine, 5-chloro-6-(2,4,6-trifluorophenyl)-7-(2-methoxyphenylthio)-[1,2,4]triazolo[1,5-a]pyrimidine, 5-chloro-6-(2,4,6-trifluorophenyl)-7-(4-methoxyphenylthio)-[1,2,4]triazolo[1,5-a]pyrimidine, 5-chloro-6-(2,4,6-trifluorophenyl)-7-(2-chlorophenylthio)-[1,2,4]triazolo[1,5-a]pyrimidine, 5-chloro-6-(2,4,6-trifluorophenyl)-7-ethoxy-[1,2,4]triazolo[1,5-a]pyrimidine 5-chloro-6-(2,4,6-trifluorophenyl)-7-cyclopentyloxy-[1,2,4]triazolo[1,5-a]pyrimidine, and 5-chloro-6-(2,4,6-trifluorophenyl)-7-(2,2,2-trifluoroethoxy)-[1,2,4]triazolo[1,5-a]pyrimidine.

9. A fungicidal composition which comprises a carrier, and as an active agent, at least one compound of formula I as defined in any of claims 1 or 5 or 6 or 7 or 8.

10. A process for the preparation of a compound of formula I as defined in any of claims 1 to 4, which comprises (a) reacting a compound of the general formula II

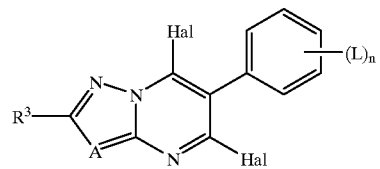

in which each of $R^3$, A, L and n have the meaning given for formula I, and Hal represents a halogen atom, with a compound of formula III $$R^1-XH \quad (III)$$

in which $R^1$ and X have the meaning given for formula I, in the presence of a base; and (b) optionally treating the resulting 5-halogentriazolopyrimidine with an alcohol, thiol or amine of formula $R^4$—YH, in which $R^4$ and Y have the meaning given for formula I, in the presence of a base.

11. A method of combating fungus at a locus which comprises treating the locus with a compound of formula I as defined in any of claims 1 or 5 or 6 or 7 or 8.

* * * * *